United States Patent [19]
Milverton

[11] Patent Number: 6,068,643
[45] Date of Patent: May 30, 2000

[54] DEVICE FOR DILATING A PUPIL AND/OR MAINTAINING A PUPIL IN A DILATED STATE

[75] Inventor: Edward John Milverton, Sydney, Australia

[73] Assignee: Milvella Pty. Ltd., Macmasters Beach, Australia

[21] Appl. No.: 09/209,370

[22] Filed: Sep. 25, 1998

Related U.S. Application Data

[63] Continuation-in-part of application No. PCT/AU96/00170, Mar. 26, 1996.

[51] Int. Cl.⁷ ............................................. A61B 17/56
[52] U.S. Cl. ......................................... 606/191; 606/107
[58] Field of Search ........................... 606/191, 107–108, 606/198, 161–162; 623/198

[56] References Cited

U.S. PATENT DOCUMENTS

| | | | |
|---|---|---|---|
| 3,991,426 | 11/1976 | Flom et al. | 606/107 |
| 4,988,357 | 1/1991 | Koss | 623/11 |
| 5,163,419 | 11/1992 | Goldman | 606/107 |
| 5,283,063 | 2/1994 | Freeman | 606/191 |
| 5,299,564 | 4/1994 | Sabatino | 606/198 |
| 5,318,011 | 6/1994 | Federman et al. | 606/107 |
| 5,322,054 | 6/1994 | Graether | 606/107 |
| 5,374,272 | 12/1994 | Arpa et al. | 606/191 |

*Primary Examiner*—Michael Buiz
*Assistant Examiner*—Jonathan D. Goldberg
*Attorney, Agent, or Firm*—Gottlieb, Rackman & Reisman, P.C.

[57] ABSTRACT

A device for dilating a pupil and/or maintaining a pupil in a dilated state. The device includes a generally arcuate body having first and second ends. The outer peripheral edge of the body has an engaging formation adapted to engage the inner peripheral edge of an iris to retain the pupil in an expanded state, and at least one positioning arm extending generally outwardly from one of the ends of the body so as to remain external to the eye.

22 Claims, 12 Drawing Sheets

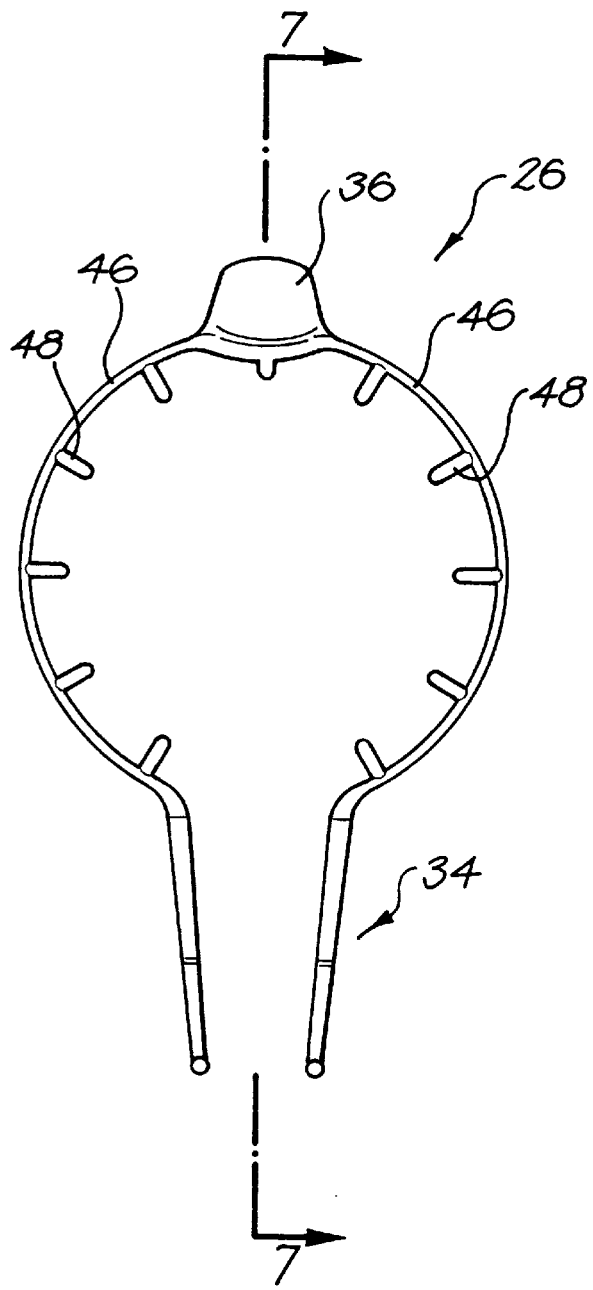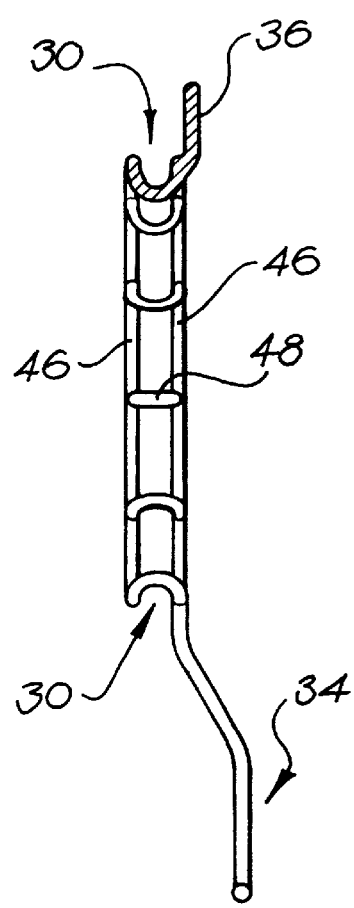
FIG. 6
FIG. 7

DEVICE FOR DILATING A PUPIL AND/OR MAINTAINING A PUPIL IN A DILATED STATE

CROSS-REFERENCE TO RELATED APPLICATIONS

This application is a continuation-in-part of International (PCT) Patent Application No. PCT/AU96/00170, filed on Mar. 26, 1996, and designating the United States, which claimed priority to Australian Patent Applications Ser. No. PN 2010, filed Mar. 27, 1995 and Ser. No. PN 4627, filed Aug. 7, 1995.

FIELD OF THE INVENTION

The present invention relates to a device for dilating a pupil and/or maintaining a pupil in a dilated state.

The invention has been developed primarily for use in ophthalmic surgery and will be described hereinafter with reference to this application. However, it will be appreciated that the invention is not limited to this particular field of use and can be utilised in other medical procedures where an opening is required to be expanded and maintained in the expanded state.

BACKGROUND OF THE INVENTION

It is advantageous in many ophthalmic surgical procedures for the pupil to be dilated as much as possible. A pupil is dilated when the iris retracts towards the outer edges of the eye. This normally occurs when the eye is deprived of bright light, for example, at night.

When performing ophthalmic operations, such as replacing the lens of a patient's eye with an artificial intraocular lens, a dilated iris and pupil gives the surgeon a larger area to manipulate surgical instruments in order to operate on the human lens. The more area available to the surgeon reduces the risk of damaging the iris or other components of the eye due to unintentional contact with the surgical instruments.

A common method of dilating the pupil is the use of chemical eyedrops. The eyedrops are formulated to trigger the expansion of the iris, resulting in a dilated pupil. However, such eyedrops are not effective on all patients and more surgically complicated measures are often required. Also, such eyedrops can "wear off" during an operation resulting in the iris retracting and reducing the pupil size.

One method to dilate and maintain a pupil in the dilated state involves making four minor incisions at roughly 90° intervals around the periphery of the cornea and inserting a small hook-like apparatus through each incision. The hooks engage with the inner circumferential edge of the iris and when retracted, pull the iris outwards to define an enlarged substantially square shaped opening. Another method, known as a sphincterotomy, involves making an incision into the cornea through which a blade is passed that makes radial cuts into the iris itself, thus allowing the iris to dilate and expose more of the lens. Both the above methods add extra time to the actual operation being performed and the latter involves considerable risk or damage to the patients iris. Moreover, the damage done in segmenting the iris during a sphincterotomy is irreversible and results in a permanently disfigured iris.

It is an object of the invention, to overcome or ameliorate at least some of the deficiencies of the prior art.

SUMMARY OF THE INVENTION

According to a first aspect of the invention there is provided a pupil dilating device for dilating a pupil and/or maintaining a pupil in a dilated state, said device including a generally arcuate body made of a resilient material and having first and second ends, an outer peripheral edge of the body having an engaging formation adapted to engage the inner peripheral edge of an iris to retain the pupil in an expanded state, and two integrally formed positioning arms each extending generally outwardly from one of said first and second ends of the body respectively, so that the distal portions of the positioning arms remain external to the eye.

Preferably also, the body is adapted to deform to a generally elongated or folded configuration able to be passed through an exterior incision in the eye and resiliently return to a substantially annular configuration engaging the iris edge.

In one embodiment, a bridge member extends between the positioning arms, such that the arms are prevented from crossing over each other in a scissor type action when the dilating device is deformed into its folded configuration. Preferably, the bridge member is pivotally mounted at its ends to the positioning arms and includes a central hinge such that the positioning arms may be drawn towards each other to deform the dilating device into the folded configuration.

Desirably, the body also includes a guide tab extending outwardly from and generally parallel to a diameter of the body for aiding insertion of the device, for supporting the body in engagement with the iris edge and also for preventing the body from "falling" through the pupil opening.

In a preferred embodiment, the positioning arm or arms each terminate in a gripping formation. The formation provides a convenient gripping point for the device and also, if so desired, allows the positioning arms to be sutured to the eye. The gripping formation or formations may include a hole through which a suture thread may be passed.

In another preferred embodiment, each of the arm or arms includes a proximal portion adjacent the body that extends close to the plane of the surface of the iris and a distal portion that is off-set in a direction away from the plane of the iris and which extends to the gripping formation or formations so as to allow the distal portion or portions to remain external to, but closely adjacent the surface of the eye whilst the device is in use dilating the pupil.

The resilience of the body preferably provides a radially outwardly directed force capable of urging into and maintaining the body in a substantially annular configuration whilst engaging the iris to expand and/or maintain the pupil in the dilated state.

In a preferred form, the engaging formation is desirably formed so as to define a continuous recessed channel between the ends.

In a further embodiment, the body comprises a pair of circumferentially aligned parallel axially spaced apart incomplete rings and a series of circumferentially spaced apart curved joining members extending from one ring to the other to define said engaging formation.

In another embodiment, the body is provided with a plurality of radially outwardly angled pairs of reaps, each pair of flaps defining a portion of the recess therebetween.

The body is preferably made from a material selected from the group including prolene, poly methyl methacrylate, nylon, silastic, silicone polyimide, polyamide or a combination thereof, or any other material having the requisite properties of resilience and suitability for use in surgical procedures.

In a further embodiment, an insert of a second material is contained within the body to give the required resilience.

In a further embodiment, the body is sized to provide an inner diameter in the substantially annular configuration of between approximately 5.5 mm and 7 mm, the body itself has a radial thickness of between about 0.75 and 1.25 mm. In this embodiment, the recess has an axial depth of about 1.12 mm and the guide tab extends from the outer edge of the body by about 1.25 mm. The distal portions of the arms are preferably offset from the proximal portions by about 1.5 to 2.0 mm in the axial direction.

In yet another embodiment, regions of weakness may be included in the body to further facilitate resilient deformation between the expanded annular and the elongated or folded configurations.

Desirably, the device is tinted for increased visibility to the surgeon.

In the annular configuration, the arcuate body preferably has an included angle of between approximately 270° and 340°.

BRIEF DESCRIPTION OF THE DRAWINGS

Preferred embodiments of the invention will now be described, by way of example only, with reference to the accompanying drawings in which;

FIG. 6 is a plan view of a second embodiment of the invention;

FIG. 7 is a sectional side view of the device shown in FIG. 6;

PREFERRED EMBODIMENTS OF THE INVENTION

Figure 1:
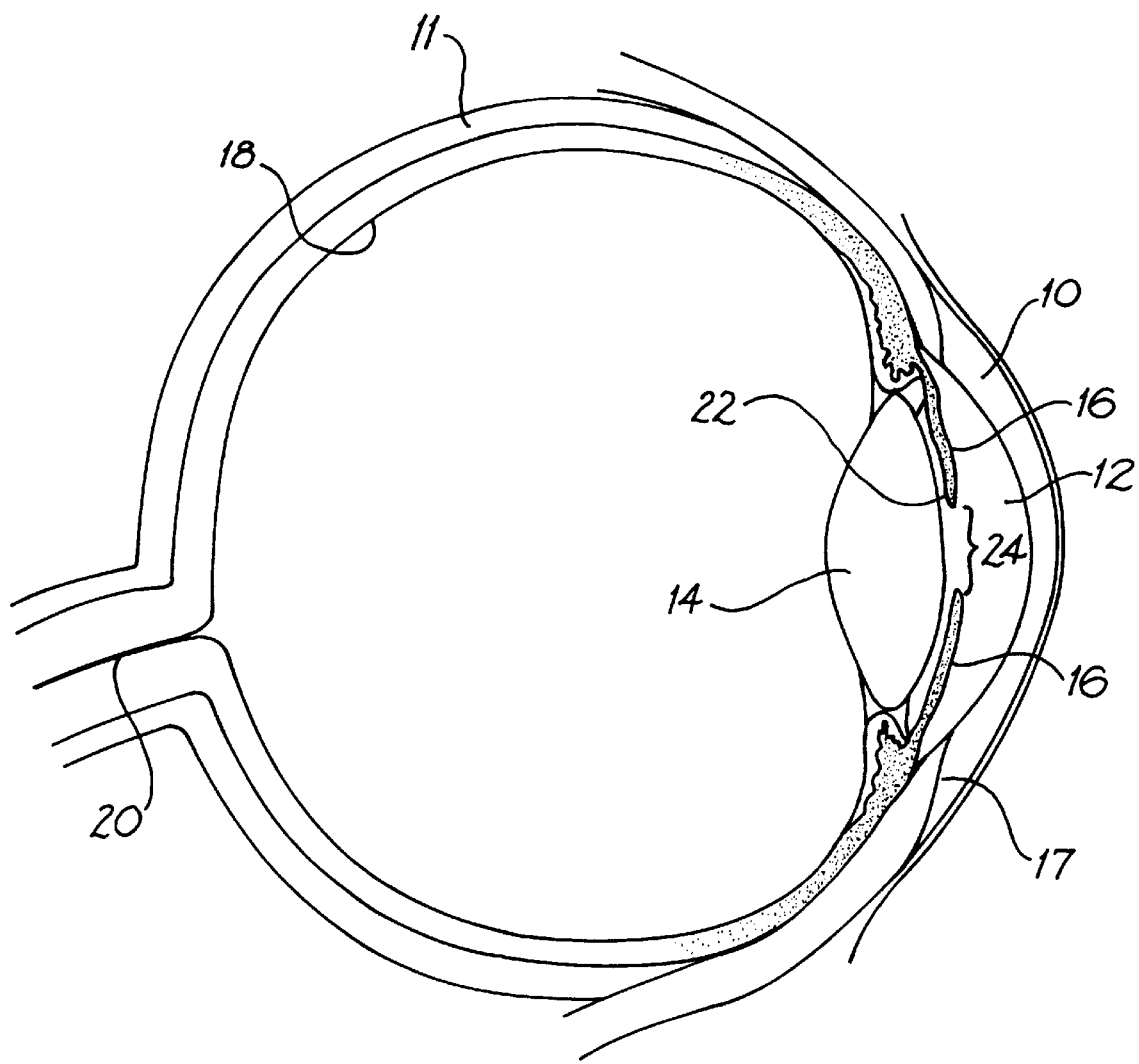
FIG. 1 is a sectional side view of a human eye.

Referring to FIG. 1 there is shown a human eye having a cornea 10, sclera 11, anterior chamber 12, lens 14, iris 16, limbus 17, retina 18 and optic nerve 20. The iris 16 has an inner peripheral edge 22, the boundary of which defines the opening of the known as the pupil 24 (the black circle in the centre of an eye).

As described previously, it is advantageous during surgery of the eye, for the pupil opening 24 to be as large as possible to permit access to the lens and other parts of the eye via incisions in the cornea or sclera.

Figure 2:
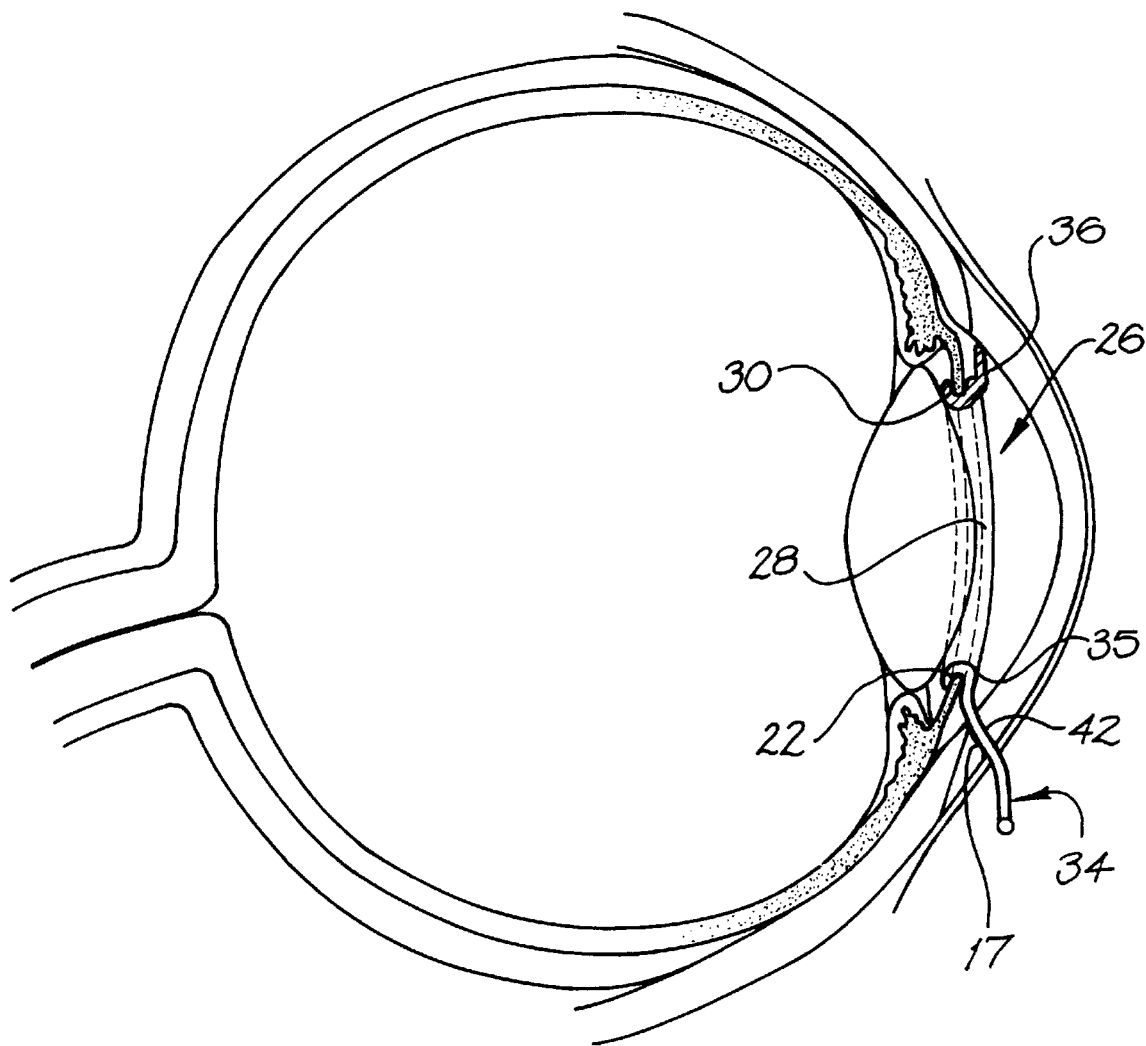
FIG. 2 is a sectional side view of the eye shown in FIG. 1 showing the pupil being maintained in a dilated state by a first embodiment of the device according to the invention.

Referring to FIG. 2, there is shown in use a device 26 according to the invention for dilating the pupil and/or maintaining the pupil in the dilated state. The device 26 comprises a generally arcuate body 28 having first and second ends 35. The outer peripheral edge of the body has a recess 30 adapted to engage the inner peripheral edge 22 of the iris to retain the pupil in a dilated state. The device also includes positioning arms 34 which extend generally outwardly from the ends 35 of the body and remain external to the eye when the device is in use. The arms are more clearly shown in FIGS. 3 and 4. The recess 30 forms a continuous channel 32 between the ends 35. Device 26 also includes guide tab 36 which extends from the body 28.

Figure 3:
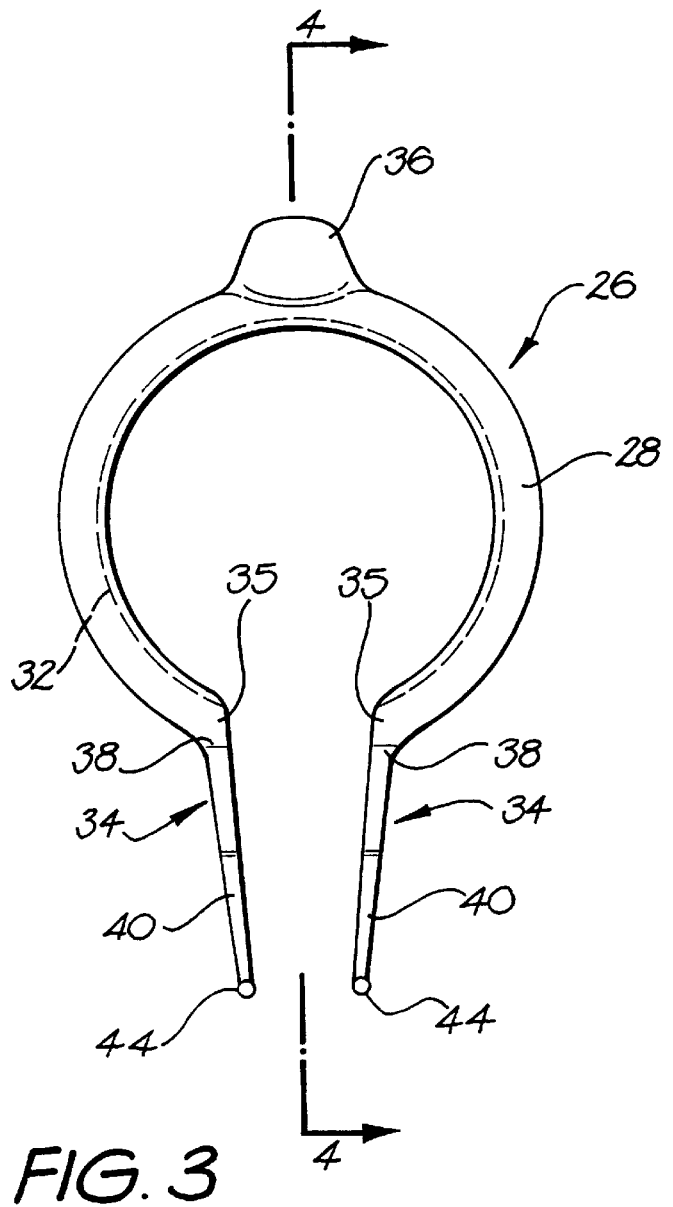
FIG. 3 is a plan view of the device shown in FIG. 2 illustrated in an annular configuration.
Figure 4:
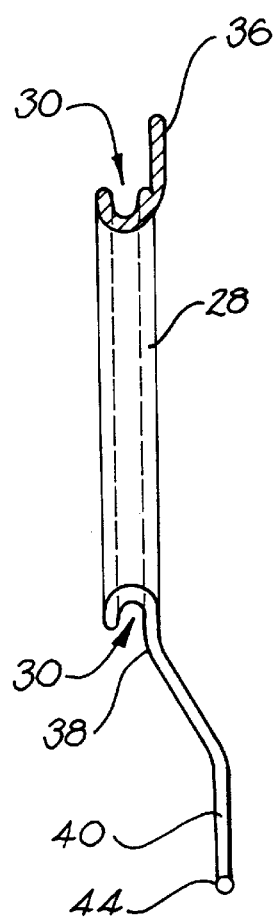
FIG. 4 is a side view of the device shown in FIG. 3.

Referring to FIGS. 3 and 4, the arms 34 can each be seen to include a proximal portion 38 adjacent to the body and a distal portion 40 substantially parallel to, but offset from the proximal portion 38. The arms 34 terminate in gripping formations 44.

If desired, the formations 44 also allow the surgeon to suture the arms 34 to the sclera 11. Holes can be provided through the formations through which the suture thread may be passed.

Figure 5:
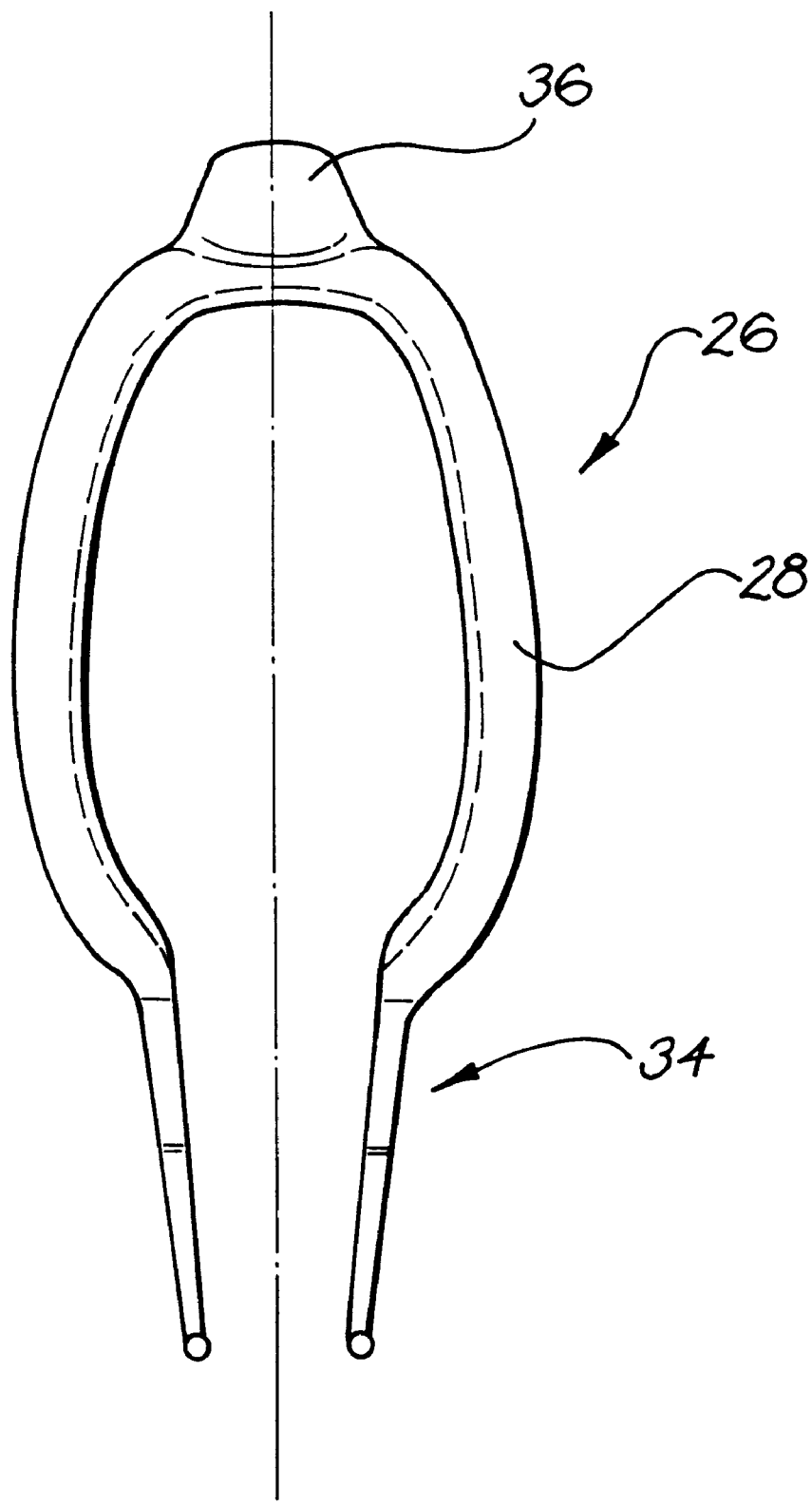
FIG. 5 is a plan view of the device shown in FIG. 3 in the elongated or folded configuration.

Referring in particular to FIG. 5, it can be seen that the body 28 is adapted to resiliently deform to a generally elongated or folded configuration as shown which is able to be passed through an exterior incision into the eye and, upon release, return to a substantially annular configuration, as shown in FIG. 4. Referring next to FIGS. 6 to 10, there are shown several alternative embodiments of the device according to the invention.

The embodiment of the device shown in FIGS. 6 and 7 comprises a pair of circumferentially aligned parallel axially spaced-apart incomplete rings 46 with a series of circumferentially spaced-apart joining members 48 extending from one ring to the other to define the recess 30.

Figures 8, 9:
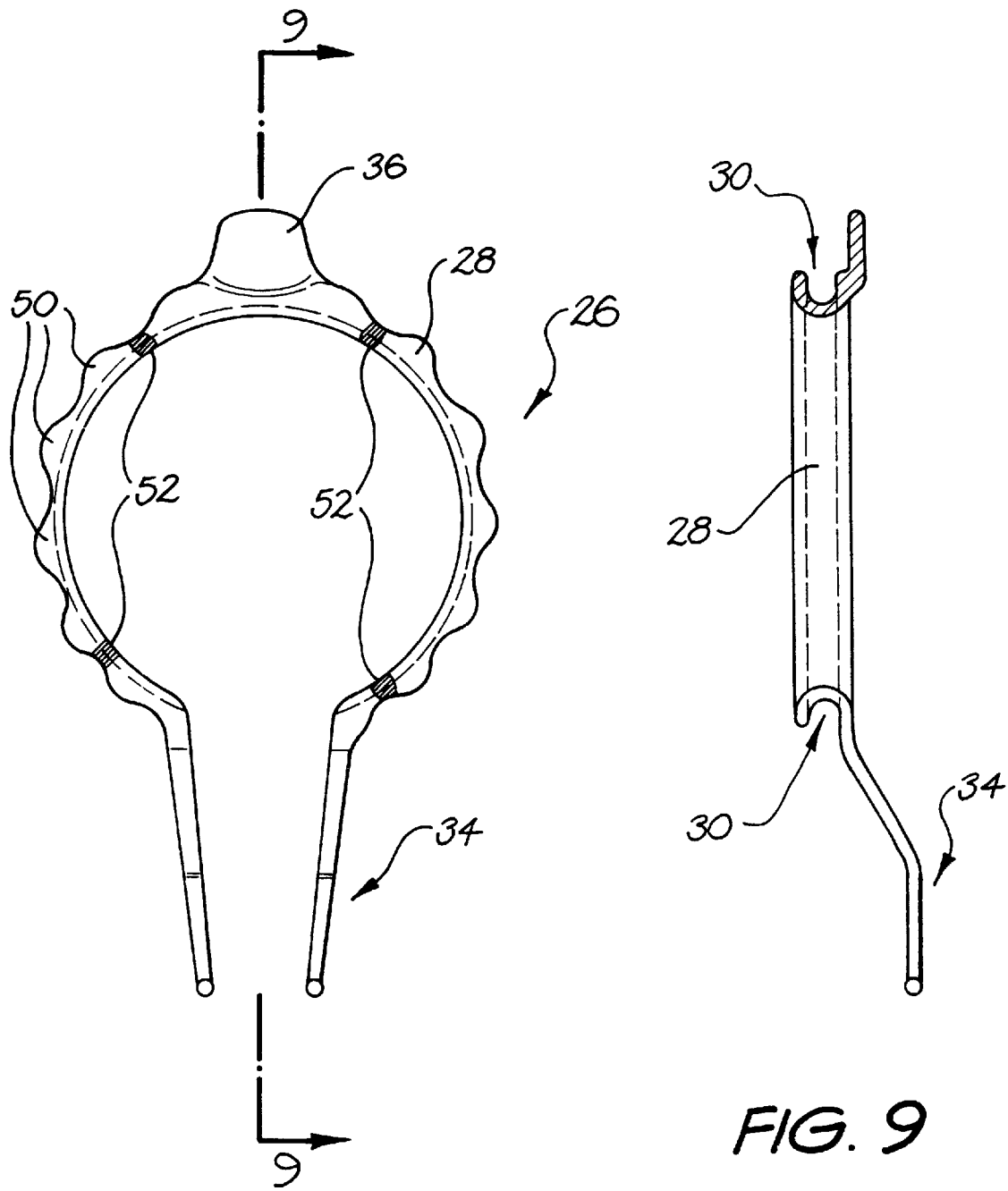
FIG. 8 is a plan view of a third embodiment of the invention.
FIG. 9 is a sectional side view of the device shown in FIG. 8.

The embodiment of the invention shown in FIGS. 8 and 9 is similar to the previously illustrated embodiments except that the body 28 is provided with a series of radially extending flaps 50 around its periphery. Furthermore, this embodiment includes regions of weakness 52 which facilitate resilient deformation between the configurations shown in FIG. 3 and FIG. 5.

Figures 10, 11:
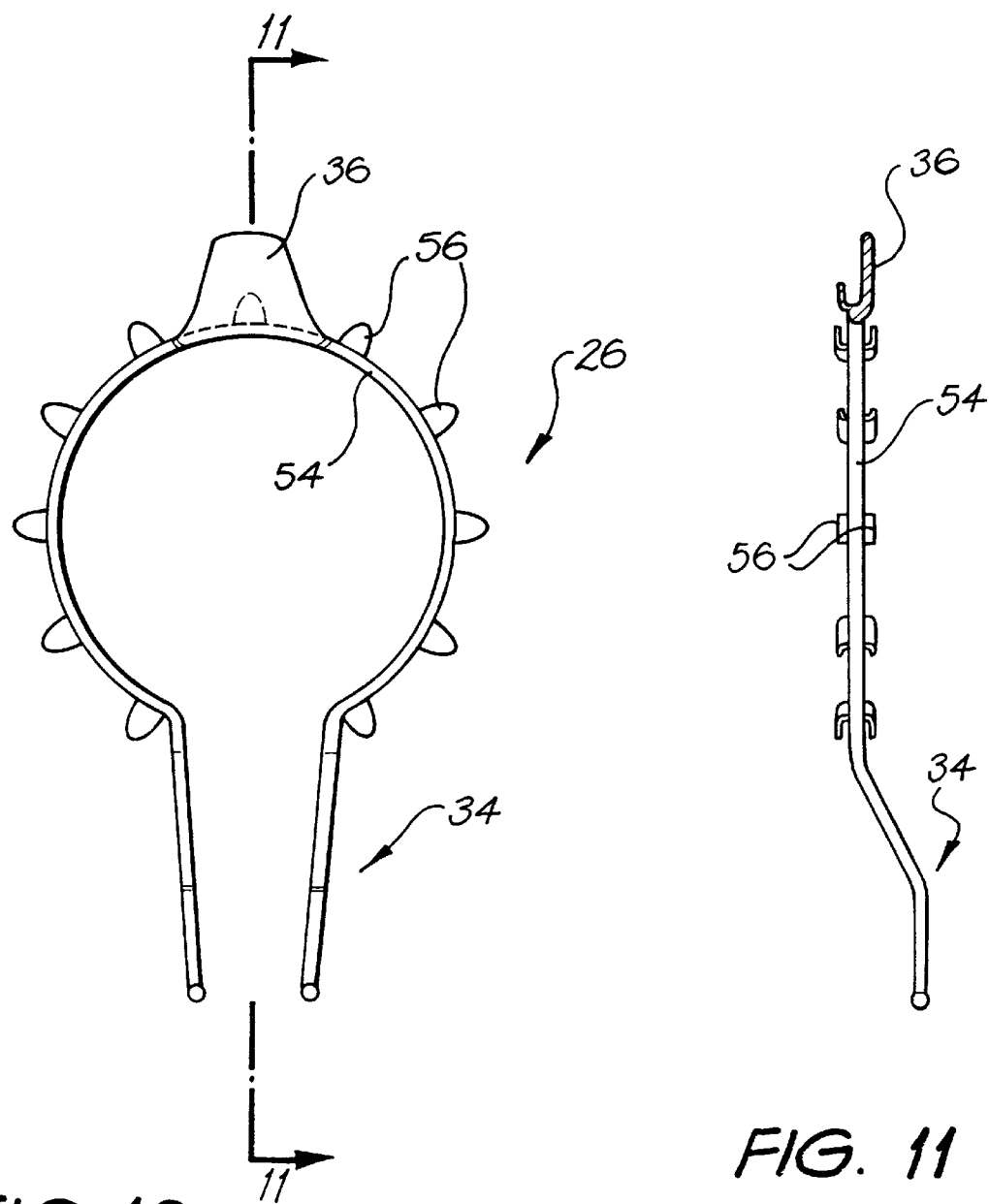
FIG. 10 is a plan view of a fourth embodiment of the invention.
FIG. 11 is a sectional side view of the device shown in FIG. 10.

Referring now to the embodiment shown in FIGS. 10 and 11, the body of the device is in the form of a single incomplete annular ring 54 provided with a plurality of radially outwardly angled pairs of flaps 56. Each pair of flaps defines a portion of the recess 30 therebetween.

Figure 12:
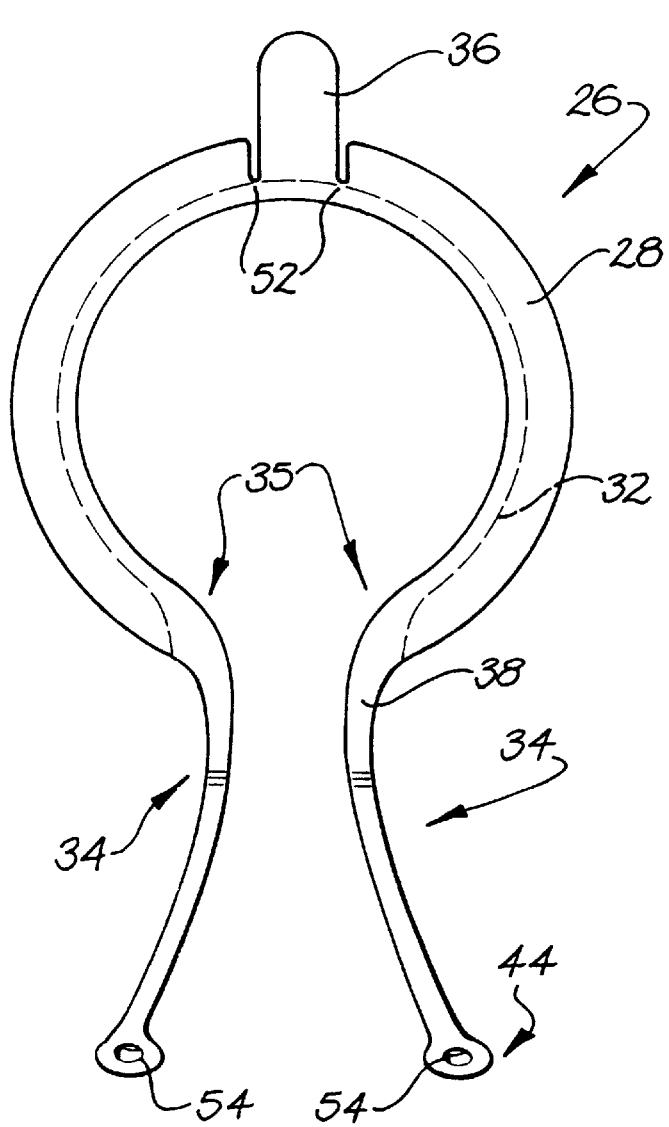
FIG. 12 is a plan view of a fifth embodiment of the invention.
Figure 13:
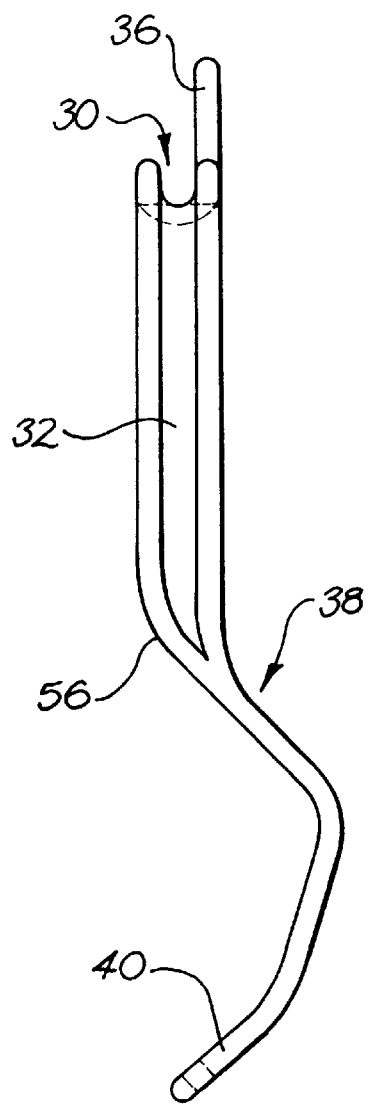
FIG. 13 is a side view of the device shown in FIG. 12.
Figure 14:
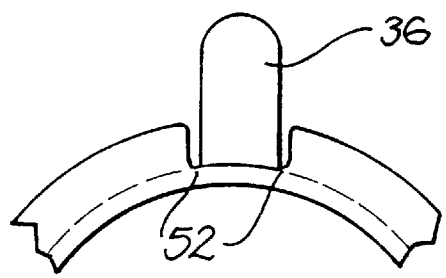
FIG. 14 is an inverted partial plan view of the device shown in FIG. 12.
Figure 15:
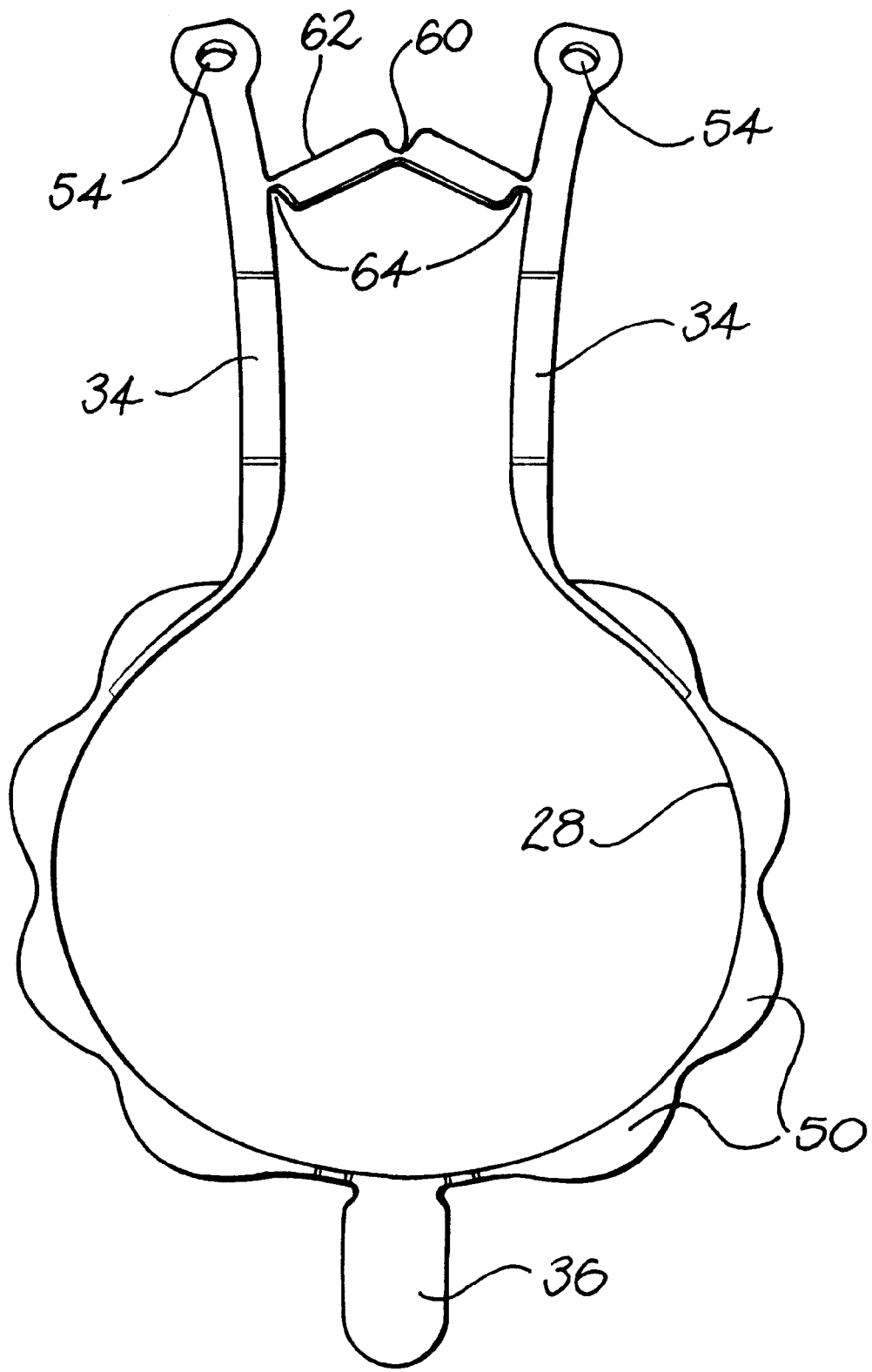
FIG. 15 is a top plan view of a sixth embodiment of the invention.
Figure 16:
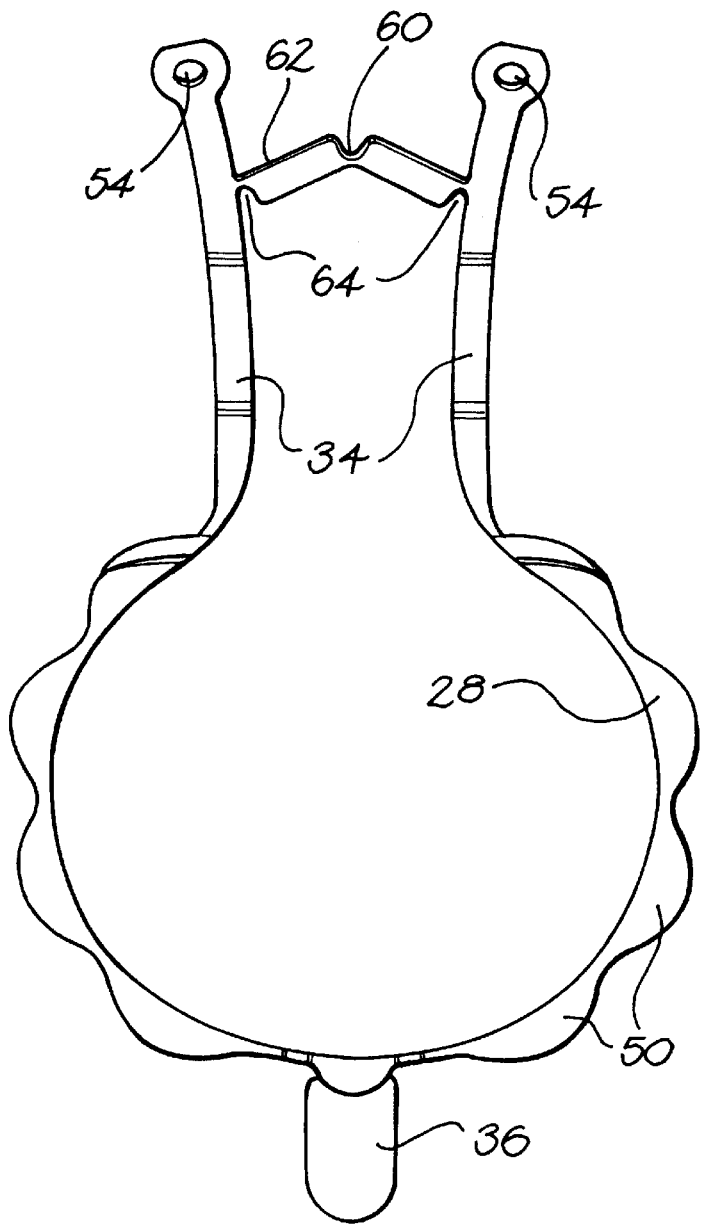
FIG. 16 is a bottom plan view of the sixth embodiment of the invention.
Figure 17:
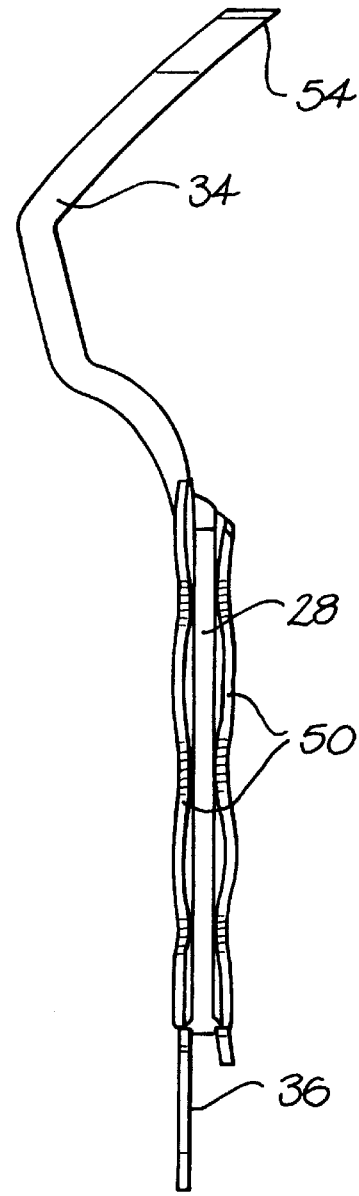
FIG. 17 is a right side elevation of the sixth embodiment of the invention.
Figure 18:
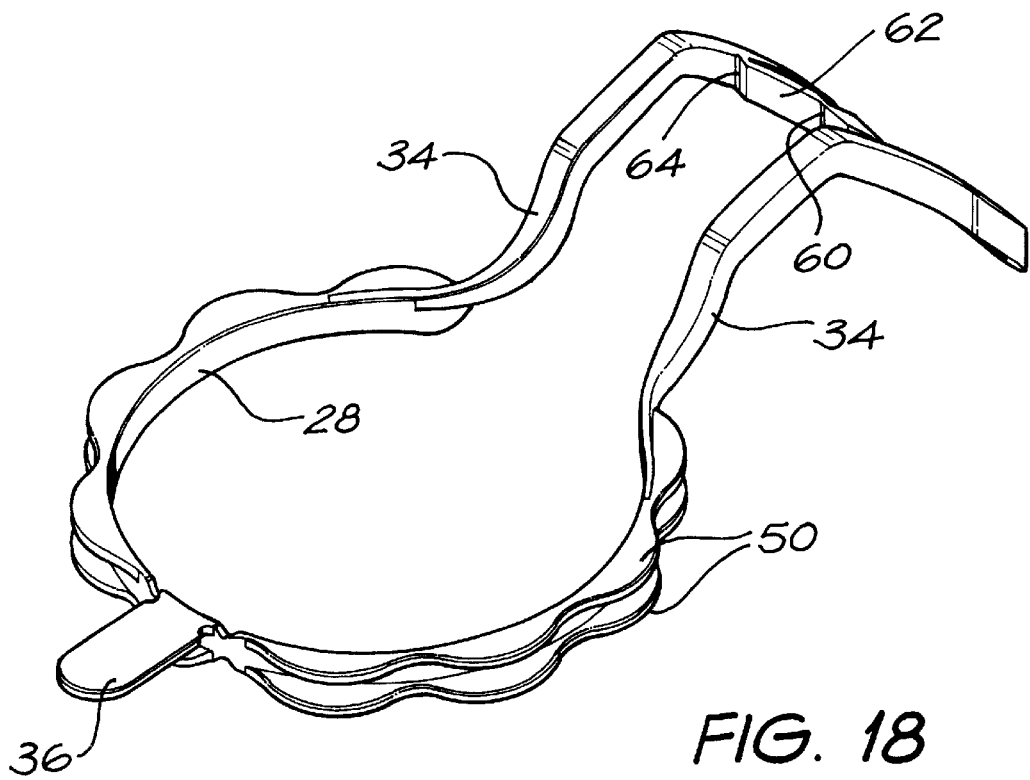
FIG. 18 is a perspective view showing the top and right side of the sixth embodiment of the invention.
Figure 19:
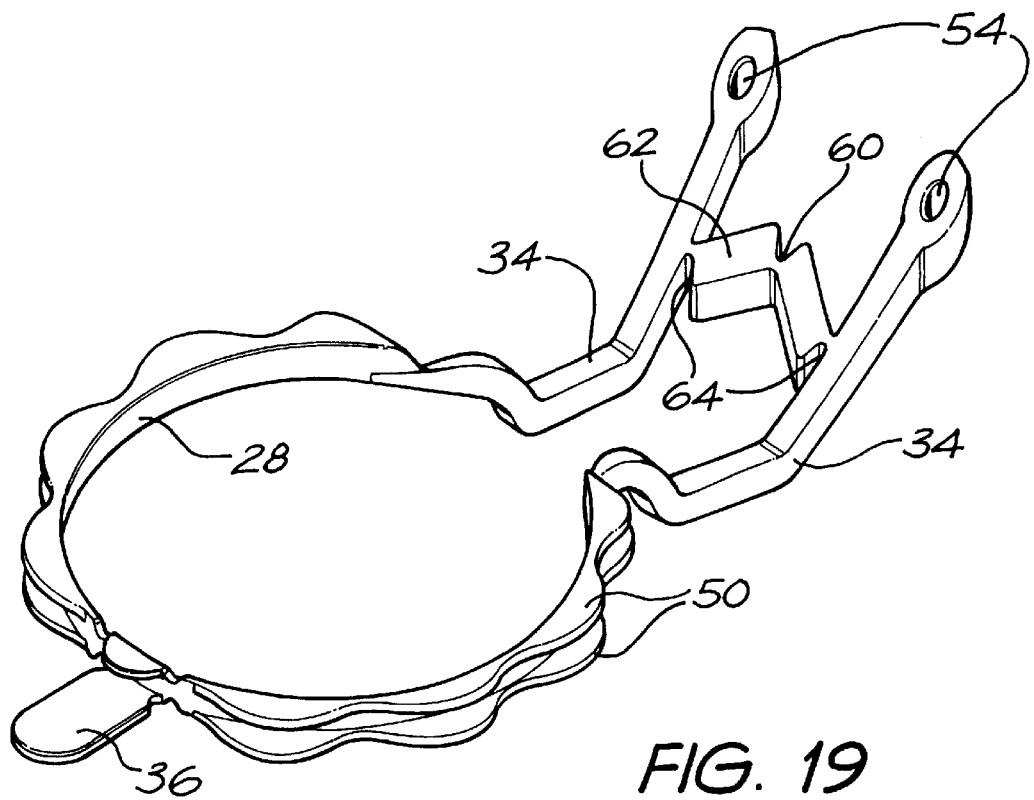
FIG. 19 is a perspective view showing the bottom and left side of the sixth embodiment of the invention.
Figure 20:
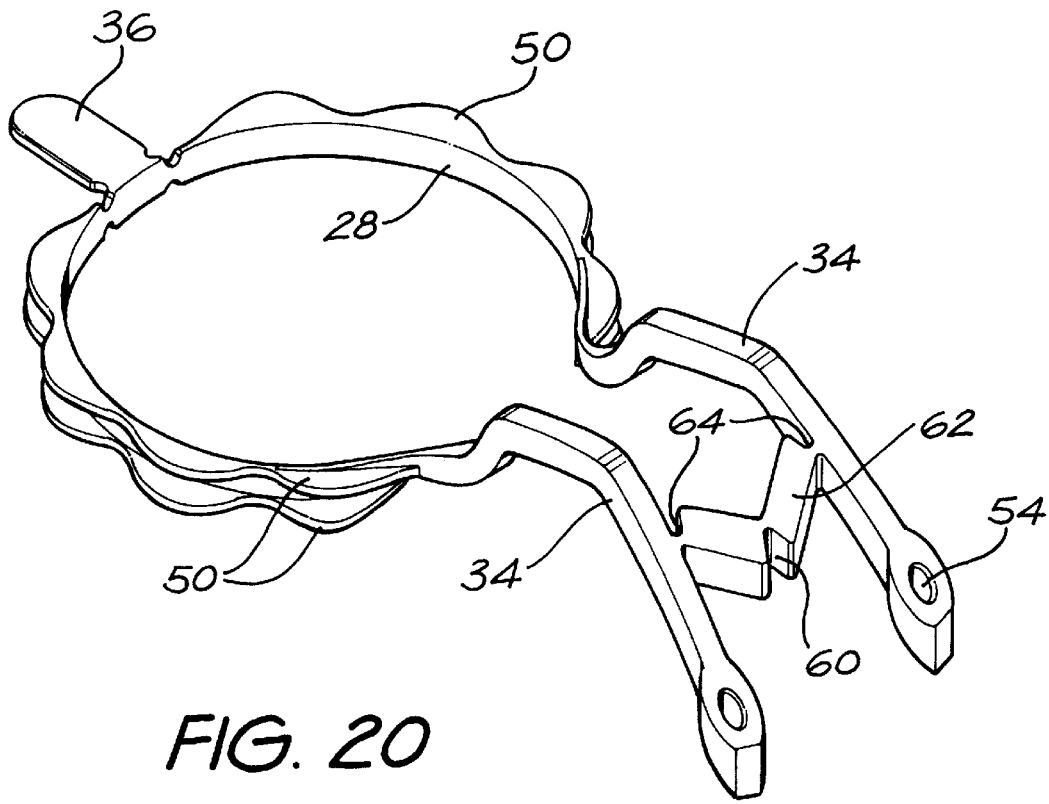
FIG. 20 is a perspective view showing the rear and right side of the sixth embodiment of the present invention.
Figure 21:
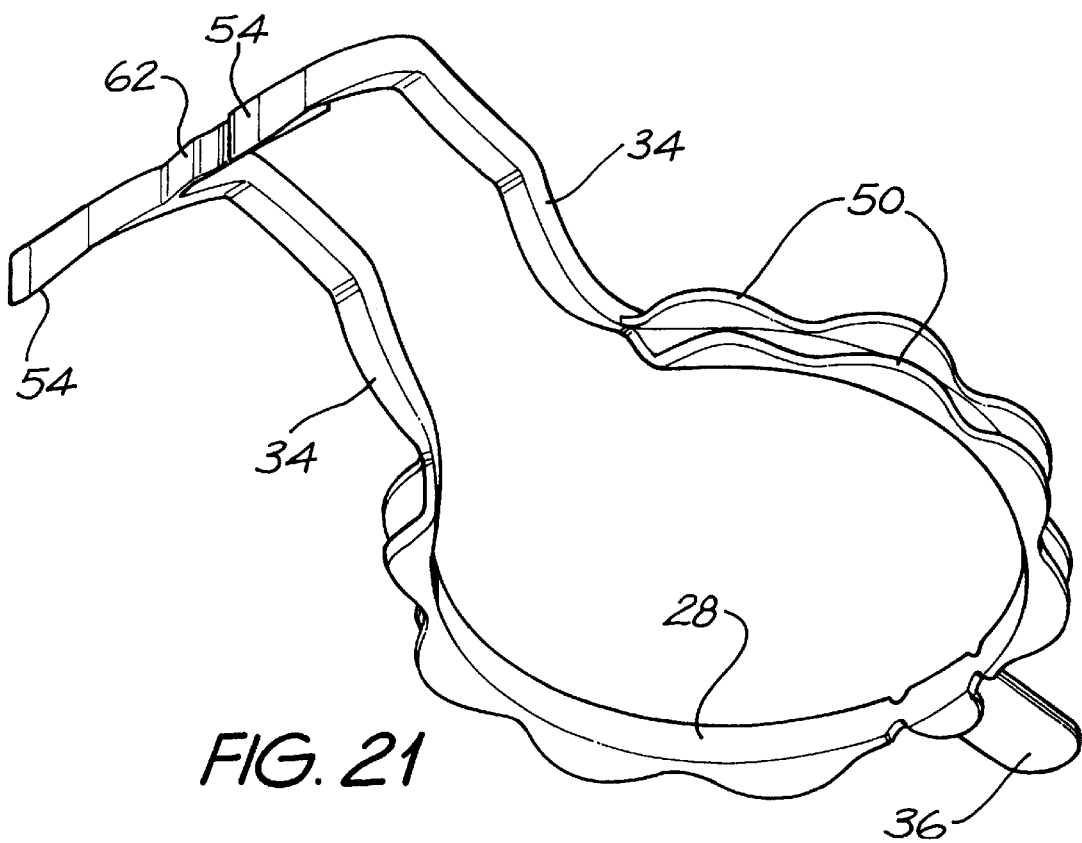
FIG. 21 is a perspective view showing the bottom and left side of the sixth embodiment of the present invention.

A fifth embodiment of invention is shown in FIG. 12 to 14. This embodiment is similar to those previously described except the distal portions 40 of each of the arms 34, which remain external the eye during use, are angled slightly downwardly towards the eye surface to prevent the device from tilting towards the cornea when the arms are pressed downwards. To allow easier suturing, the gripping formations 44 are each provided with a pre-formed suture hole 54 which is adapted to receive suture thread therethrough.

When viewed in plan, the arms 34 are angled slightly outwardly from the incision which, in addition to the downward angling, provides extra clearance for instruments passing through the incision. Also, the shape of the arms allows the device to maintain a snug fit with the eye when in use dilating the pupil.

Additionally, as best shown in the inverted plan view of FIG. 14, the body 28 of the device is recessed below the guide tab 36 so as to provide two regions of weakness 52 which facilitate flexure of the device into the elongated position described previously.

Further, to enhance the withdrawal of the device, the proximal portion 38 of each of the arms 34 is provided with a smoothly tapered surface 56. This lessens the likelihood of the device snagging or catching as the device is withdrawn through the incision.

Referring back to FIG. 2, there is shown a tunnel incision 42 used in, for example, a lens replacement. The circumferential incision begins generally just behind the limbus 17, is 2.5 to 5.5 mm wide, and extends normally into the sclera for about half it's depth (approximately 0.5 to 0.75 mm). The incision then travels through the sclera and then cornea for approximately 3 to 4 mm then again is angled through the cornea to finally open into the anterior chamber 12.

In use of the device, the incision 42, of approximately 2.5 to 5.5 mm in width, is made through the cornea and/or sclera of the eye. The device 26 is then elongated or folded so that it can more easily be passed through this tunnel incision into the anterior chamber 12 of the eye. The device may be inserted in the elongated configuration by forceps such as angled "McIntyre" forceps. The forceps grip the device in recess 30 and so elongate the device for passing it through the incision. The guide tab 36 aids the insertion process.

Preferably, the anterior chamber is filled with a viscoelastic fluid prior to insertion of the device. As the device is being passed through the incision, the inner peripheral edge 22 of the iris is partially located in recess 30. This location is helped by guide tab 36 sliding over, and resting upon, the upper surface of the iris. The guide tab 36 also prevents the device from "falling" through the pupil opening during insertion.

Once through the incision the resilience of the device then returns it to the substantially circular configuration shown in FIG. 3. As the device filly engages edge 22 in recess 30 it provides sufficient radial force to expand the iris, thus dilating the pupil. This radial force is also sufficient to maintain the pupil in the dilated state shown in FIG. 2.

It will be appreciated that due to the small size of both the device and the iris, that occasionally some misengagement may occur which can be corrected by repositioning the device using arms 34. As a portion of each arm remains external to the eye during pupil dilation, this repositioning can readily be effected. Also, the surgeon can give additional dilation to the eye by pushing the arms towards the eye centre. Since the proximal and distal portions, 38 and 40 respectively, are offset axially from one another, the device can easily be positioned parallel to, and adjacent with, the iris edge after the proximal portions have passed through the incision in the eye. The surgical incision is generally offset so as to be above the plane of the iris edge.

The apparatus according to the invention provides several major advantages over existing methods of dilating pupils. The first is that it will dilate and hold in a dilated position a pupil that would not otherwise dilate under the influence of eyedrops and the like. This gives the surgeon the space needed to perform the eye operation without having to resort to more drastic measures to dilate the pupil. Moreover, since the device is introduced into the anterior chamber of the eye by a single incision, there is minimal surgical trauma to the patient.

Another advantage is that the device can be introduced through the usual incision made for surgery. This allows the device to be used without any additional incisions being made in the patients eyes. The incision may have to be made slightly wider than normal to fit both the arms and also tools such as a phaco-emulsifier simultaneously through the incision.

A further advantage provided by the device according to the invention is that whilst maintaining the pupil in the dilated state, the device serves to effectively guard the delicate edge of the iris against unintentional contact with surgical instruments.

A yet further advantage of the device of the invention is provided by arms 34 remaining partially external to the eye whilst the device is being used. This allows easy re-positioning of the device and, more importantly, allows removal of the device generally without introducing any surgical tools into the anterior chamber. This greatly reduces the risk of damaging the eye during surgery. Additionally, formations 44 provide a convenient gripping point for a surgeon removing the device and also allow the device to be sutured in the correct position whilst an operation is performed. This can be important when surgical tools are continually being passed in and out of the incision which may otherwise accidentally move or dislodge the device.

For reasons of convenience and sterilisation, the device will preferably be disposable.

The device can be manufactured in many sizes to cater for varying eye sizes including, for example, animal eyes.

A sixth embodiment of the invention is shown in FIGS. 15 to 21. This embodiment is similar to those previously described except the distal portions of each of the positioning arms 34 which remain external to the eye during use include a hinged bridge arrangement 62 pivotally connected via weakened portions 64 to each arm. Another weakened portion 60 is provided in the center of the bridge arrangement 62. When the arms are drawn towards each other to form the elongate or folded configuration needed for insertion into the eye the bridge arrangement 62 prevents the arms 34 from crossing over one another in a scissor action This allows the surgeon to maintain more control over the positioning of the device during insertion and removal. As in the fifth embodiment, the positioning arms are angled slightly downwardly towards the eye surface to prevent the device from tilting towards the cornea when the arms are pressed downwardly. Preformed suture holes 54 are provided for easier suturing.

From the above, it will be appreciated that the device according to the invention represents significant improvements over the previously used techniques and devices for dilating a pupil and maintaining it in a dilated state.

Although the invention has been described with reference to specific examples, it will be appreciated by those skilled in the art that the invention may be embodied in many other forms.

I claim:

1. A pupil dilating device for dilating the pupil of a human eye and/or maintaining a pupil in a dilated state, said device comprising:
   a) a generally arcuate body made of a resilient material and having first and second ends and an outer peripheral edge, the edge of the body having an engaging formation adapted to engage an inner peripheral edge of an iris to retain the pupil in an expanded state; and
   b) at least one integral positioning arm extending generally outwardly from one of said first and second ends of the body, so that a distal portion of the positioning arm remains external to the eye.

2. The device as claimed in claim 1, said device having two integrally formed positioning arms each extending generally outwardly from one of said first and second ends of the body respectively, so that the distal portions of the positioning arms remain external to the eye.

3. The device as claimed in claim 1 wherein the body is adapted to deform to a generally elongated or folded configuration able to be passed through an exterior incision in the eye and resiliently return to a substantially annular configuration engaging the iris edge.

4. The device as claimed in claim 3 wherein regions of weakness are included in the body to further facilitate resilient deformation between the expanded annular and the elongated or folded configuration.

5. The device as claimed in claim 3 wherein the arcuate body defines, between the first and second ends, an included angle of between approximately 270° and 340°.

6. The device as claimed in claim 1 wherein a bridge member extends between the positioning arms such that the arms are prevented from crossing over each other.

7. The device as claimed in claim 6 wherein the bridge member is pivotally mounted at respective ends to the positioning arms and includes a central hinge such that the positioning arms may be drawn towards each other to deform the device into the generally elongated or folded configuration.

8. The device as claimed in claim 1 wherein said at least one positioning arm terminates in a gripping formation.

9. The device as claimed in claim 8 wherein the gripping formation includes a hole through which a suture thread may be passed.

10. The device as claimed in claim 1 wherein the body also includes a guide tab extending outwardly from and generally parallel to a radius of said generally arcuate body for aiding insertion of the device and for supporting the body in engagement with an edge of the iris.

11. The device as claimed in claim 10 wherein the guide tab extends radially from the average outer most edge of the body by about 1.25 mm.

12. The device as claimed in claim 1 wherein the arm includes a proximal portion adjacent the body that extends close to the plane of the surface of the iris and a distal portion that is off-set in a direction away from the plane of the iris and which extends to a gripping formation so as to allow the distal portion to remain external to, but closely adjacent to the outer surface of the eye whilst the device is in use dilating the pupil.

13. The device as claimed in claim 1 wherein the resilience of the body provides a radially outwardly directed force capable of urging into and maintaining the body in a substantially annular configuration whilst engaging the iris to expand and/or maintain the pupil in the dilated state.

14. The device as claimed in claim 13 wherein the distal portion of the arm is offset from a proximal portion of the arm by about 1.5 mm to 2.0 mm in an axial direction.

15. The device as claimed in claim 1 wherein the engaging formation is formed so as to define a continuous recessed channel between said ends of said body.

16. The device as claimed in claim 15 wherein the recessed channel has an axial depth of less than 1.12 mm.

17. The device as claimed in claim 1 wherein the body comprises a pair of circumferentially aligned parallel axially spaced apart incomplete rings and a series of circumferentially spaced apart curved joining members extending from one ring to the other to define said engaging formation.

18. The device as claimed in claim 1 wherein the body is provided with a plurality of radially outwardly angled pairs of flaps, each pair of flaps defining a portion of the engaging formation therebetween.

19. The device as claimed in claim 1 wherein the body is made from a material selected from the group consisting of prolene, poly methyl methacrylate, nylon, silastic, silicone polyimide, polyamide or a combination thereof, or any other material having the requisite properties of resilience and suitability for use in surgical procedures.

20. The device as claimed in claim 1 wherein an insert of a second material is contained within the body to give resilience sufficient to maintain the pupil in an expanded state.

21. The device as claimed in claim 1 wherein the body is sized to provide an inner diameter in the substantially annular configuration of between approximately 5.5 mm and 7 mm, the body itself having a radial thickness of between about 0.75 mm and 1.25 mm.

22. The device as claimed in claim 1 wherein the device is tinted for increased visibility to a surgeon.

* * * * *